United States Patent [19]

Abrevaya et al.

[11] Patent Number: 4,608,360

[45] Date of Patent: Aug. 26, 1986

[54] DEHYDROGENATION CATALYST COMPOSITIONS AND METHOD OF PREPARING SAME

[75] Inventors: Hayim Abrevaya, Chicago; Tamotsu Imai, Mount Prospect, both of Ill.

[73] Assignee: UOP Inc., Des Plaines, Ill.

[21] Appl. No.: 751,340

[22] Filed: Jul. 2, 1985

[51] Int. Cl.$^4$ .................. B01J 23/58; B01J 23/62; B01J 27/08

[52] U.S. Cl. .................. 502/226; 502/227; 502/328; 502/330; 585/660

[58] Field of Search ............... 502/226, 227, 328, 330; 585/660

[56] References Cited

U.S. PATENT DOCUMENTS

| | | | |
|---|---|---|---|
| 3,531,543 | 9/1970 | Clippinger et al. | 260/683.3 |
| 3,745,112 | 7/1973 | Rausch | 208/139 |
| 3,892,657 | 7/1975 | Wilhelm | 208/139 |
| 3,909,451 | 9/1975 | Wilhelm | 252/441 |
| 4,070,413 | 1/1978 | Imai | 260/683.3 |
| 4,486,547 | 12/1984 | Imai et al. | 502/226 X |

OTHER PUBLICATIONS

Journal of the American Chemical Society, 82, 2471, 1960.

*Primary Examiner*—W. J. Shine
*Attorney, Agent, or Firm*—Thomas K. McBride; John F. Spears, Jr.

[57] ABSTRACT

A novel catalytic composite is disclosed. Also disclosed is a use for the novel composite and a method for preparing the same. The catalytic composite comprises a Group VIII, noble metal component, a co-formed IVA metal component, an alkali metal or alkaline earth metal component and an alumina support having a surface area of from 5 to 150 m$^2$/g. Additionally the alumina support is such that less than about 18% of the total pore volume of the support is associated with pores having mean diameters of about 300 Angstroms or less and more than about 55% of the total pore volume of the support is associated with pores having mean diameters of about 600 Angstroms or more. The novel catalytic composite has particular utility as a paraffin dehydrogenation catalyst.

19 Claims, 1 Drawing Figure

DEHYDROGENATION CATALYST COMPOSITIONS AND METHOD OF PREPARING SAME

BACKGROUND OF THE INVENTION

This invention relates to the conversion of hydrocarbons, especially the dehydrogenation of dehydrogenatable hydrocarbons, in the presence of a catalytic composite. This invention also pertains to a new catalytic composite and a method of making it.

The dehydrogenation of hydrocarbons is an important commercial process. This is because of the great demand for dehydrogenated hydrocarbons for industrial processes and products. For example, dehydrogenated hydrocarbons are utilized in the manufacture of various products such as detergents, high octane gasolines, and pharmaceutical products. Plastics and synthetic rubbers are other products which may be produced through use of dehydrogenated hydrocarbons. One example of a specific dehydrogenation process is dehydrogenating isobutane to produce isobutylene which may then be polymerized to provide tackifying agents for adhesives, viscosity-index additives for motor oils and impact-resistant and anti-oxidant additives for plastics.

INFORMATION DISCLOSURE

U.S. Pat. No. 3,531,543 discloses dehydrogenating hydrocarbons with a catalyst comprising platinum, tin and neutralized metal oxide carrier. The preferred carriers are oxide materials whose intrinsic acidity is substantially neutralized by an alkali or alkaline earth metal component. Pure alumina, for example, has such intrinsic acidity. (cf. Pines and Haag, *Journal of the American Chemical Society*, 82, 2471 (1960)). For example, alumina catalyzes the skeletal isomerization of olefins, dehydrates alcohols and strongly chemisorbs amines. Also, with increasing amounts of alkali present there is a parallel decrease in these acidic alumina properties. Preferably, the carrier of this patent is a nonacidic lithiated alumina. The reference, however, does not disclose the novel composite of the present invention in that it fails to disclose a support having comparable pore distribution.

U.S. Pat. No. 3,745,112 discloses a catalyst for reforming hydrocarbons which comprises a platinum group component, a tin component and a halogen component with a porous carrier material. This patent discloses also that a platinum-tin-alkali or alkaline earth composite is a particularly effective catalyst for dehydrogenating hydrocarbons. In the dehydrogenation catalyst composite of this reference wherein the alkali or alkaline earth component is added, the amount of halogen, if not entirely eliminated, is minimized in order to minimize or neutralize the acidic functions of the alumina and halogen components which tend to promote hydrocarbon cracking and isomerization side reactions which are not desired in commercial dehydrogenation processes. This reference also does not disclose a support like that of the instant invention.

U.S. Pat. No. 3,892,657 discloses that indium is a good promoter for platinum group-containing catalysts when the atomic ratio of indium to platinum is from about 0.1:1 to about 1:1. This patent discloses also that a Group IVA component selected from the group of germanium, tin, and lead can be added to the acidic form of the indium-containing catalysts for reforming applications. The acidic form of this catalyst, then, comprises a platinum group component, a Group IVA component, an indium component, a halogen component and a porous carrier material. There is, however, no disclosure of a support like that of the invention.

U.S. Pat. No. 3,909,451 discloses a new method for making a dehydrogenation catalyst comprising a platinum component, a tin component and an alkali or alkaline earth component. In Example V this patent discloses a platinum, tin and potassium composition comprising less than 0.2 wt. % combined chloride. However, this reference does not disclose the support of the instant invention.

U.S. Pat. No. 4,070,413 discloses a catalytic composite comprising from about 0.01 to about 2 wt. % Group VIII metal and from about 0.01 to about 0.1 wt. % lithium impregnated on an alumina support, said alumina having been hydrothermally treated in steam at a temperature of from about 800° to about 1200° C. Additionally, this reference discloses that the catalyst may advantageously comprise a germanium, tin and/or lead component, with tin being preferred. Examples II and III of the reference specifically disclose catalytic composites comprising platinum, tin, lithium and alumina wherein the alumina spheres were subjected to a calcination step in air and steam at a temperature of 1050° C. The reference, however, does not disclose the novel catalyst of the instant invention. The reference is silent as to the pore distribution of the alumina support. Additionally, the reference does not disclose the use of a co-formed Group IVA metal component. The tin components of the catalysts of Examples II and III of the reference are coimpregnated with the platinum. The tin components of these catalysts are, therefore, not co-formed. Moreover, Table I of the reference discloses that the catalysts of the reference undergo a substantial change in their apparent bulk densities (ABD) upon calcination at 1050° C. Catalyst A in Table I is disclosed as having an ABD of about 0.283 g/cc. After calcination at 1050° C. Catalysts B and C were disclosed as having ABD's of 0.309 and 0.305 g/cc, respectively. As will be more fully explained hereinafter the catalyst of the present invention does not undergo a substantial change in ABD upon calcination.

The references discussed above disclose catalytic composites comprising Group VIII noble metal components, Group IVA metal components and a refractory oxide support. However, none of the references disclose an alumina support having a surface area from 5 to 150 $m^2/g$ wherein less than about 18% of the total pore volume of the support is associated with pores having mean diameters of about 300 Angstroms or less and more than about 55% of the total pore volume of the support is associated with pores having mean diameters of about 600 Angstroms or more. Nor do any of the references disclose or hint at the hereinafter established advantages attendant the use of such a support in a catalyst system comprising a Group VIII noble metal component, a Group IVA component, and an alkali or alkaline earth metal component.

OBJECTS AND EMBODIMENTS

It is, therefore, an object of the present invention to provide an improved catalytic composite and a method of making the same. A corollary objective is to provide an improved process for the conversion of hydrocarbons and especially for the dehydrogenation of hydrocarbons.

Accordingly in a broad embodiment the present invention is a catalytic composite comprising a Group VIII noble metal component, a coformed Group IVA metal component, an alkali metal or alkaline earth metal component and an alumina support having a surface area of from 5 to 150 m$^2$/g wherein less than about 18% of the total pore volume of the support is associated with pores having mean diameters of about 300 Angstroms or less and more than about 55% of the total pore volume of the support is associated with pores having mean diameters of about 600 Angstroms or more.

In an alternative embodiment the invention is a hydrocarbon conversion process comprising contacting a hydrocarbon charge stock with a catalytic composite comprising a Group VIII noble metal, a co-formed Group IVA metal component, an alkali metal or alkaline earth metal component and an alumina support having a surface area of from 5 to 150 m$^2$/g wherein less than about 18% of the total pore volume of the support is associated with pores having mean diameters of about 300 Angstroms or less and more than about 55% of the total pore volume of the support is associated with pores having mean diameters of about 600 Angstroms or more at hydrocarbon conversion conditions.

In yet another embodiment the invention is a method of preparing a catalytic composite comprising compositing a Group VIII noble metal component, a co-formed Group IVA metal component, an alkali metal or alkaline earth metal component and an alumina support having a surface area of from 5 to 150 m$^2$/g wherein less than about 18% of the total pore volume of the support is associated with pores having mean diameters of about 300 Angstroms or less and more than about 55% of the total pore volume of the support is associated with pores having mean diameters of about 600 Angstroms or more. Other objects and embodiments will become evident with the following more detailed description of the invention.

DETAILED DESCRIPTION OF THE INVENTION

To summarize, the present invention is an improved catalytic composite, method of making the same as well as a process for the use thereof. Of particular interest is the use of the catalyst of the present invention as a dehydrogenation catalyst.

As indicated above, one feature of the catalytic composite of the invention is a Group VIII noble metal component. The Group VIII noble metal may be selected from the group consisting of platinum, palladium, iridium, rhodium, osmium, ruthenium or mixtures thereof. Platinum, however, is the preferred Group VIII noble metal component. It is believed that substantially all of the Group VIII noble metal component exists within the catalyst in the elemental metallic state.

Preferably the Group VIII noble metal component is well dispersed throughout the catalyst. It generally will comprise about 0.01 to 5 wt. %, calculated on an elemental basis, of the final catalytic composite. Preferably, the catalyst comprises about 0.1 to 2.0 wt. % Group VIII noble metal component, especially about 0.1 to about 2.0 wt. % platinum component.

The Group VIII noble metal component may be incorporated in the catalytic composite in any suitable manner such as, for example, by coprecipitation or cogelation, ion exchange or impregnation, or deposition from a vapor phase or from an atomic source or by like procedures either before, while or after other catalytic components are incorporated. The preferred method of incorporating the Group VIII noble metal component is to impregnate the refractory oxide support with a solution or suspension of a decomposable compound of a Group VIII noble metal. For example, platinum may be added to the support by commingling the latter with an aqueous solution of chloroplatinic acid. Another acid, for example, nitric acid or other optional components may be added to the impregnating solution to further assist in dispersing or fixing the Group VIII noble metal component in the final catalyst composite.

Regarding the co-formed Group IVA component, it may be selected from the group consisting of co-formed components of germanium, tin, lead or mixtures thereof. A co-formed component, however, is the preferred co-formed Group IVA component. We believe the Group IVA component exists within the catalyst in an oxidation state above that of the elemental metal. The Group IVA component may be present as a compound such as the oxide, for example, or combined with the alumina support. Preferably, the co-formed Group IVA component is well dispersed throughout the catalyst. The co-formed Group IVA component generally will comprise about 0.01 to 5 wt. %, calculated on an elemental basis, of the final catalyst composite. Preferably, the catalyst comprises about 0.2 to about 2.0 wt. % co-formed Group IVA component, especially about 0.2 to about 2.0 wt. % co-formed tin.

An essential feature of the instant invention is that the Group IVA component be co-formed. By co-formed it is to be understood that it is meant that the precursor of the Group IVA component and the precursor of the alumina support are intermingled prior to formation of the alumina support. Accordingly, the Group IVA component may be co-formed with the alumina support by coprecipitation or cogelation. A preferred method of incorporating a co-formed tin component is cogelling it during preparation of the alumina support. For example, a soluble tin compound such as stannous or stannic chloride may be mixed with an alumina hydrosol. Thereafter a gelling agent such as hexamethylenetetramine is admixed with the alumina hydrosol and tin compound and the resulting mixture is dropped into a hot oil bath forming spheres comprising alumina and tin component.

A further essential feature of the present invention is an alumina support having a surface area of from 5 to 150 m$^2$/g wherein less than about 18% of the total pore volume of the support is associated with pores having mean diameters of about 300 Angstroms or less and more than about 55% of the total pore volume of the support is associated with pores having mean diameters of about 600 Angstroms or more. Although it is not fully understood why this distinct pore volume structure results in improved catalyst performance, it is believed that the improved performance is a result of enhanced intra-particle diffusion rates induced by the improved pore structure.

The alkali or alkaline earth component of the present invention may be selected from the group of cesium, rubidium, potassium, sodium and lithium or from the group of barium, strontium, calcium and magnesium or mixtures of metals from either or both of these groups. Lithium, however, is the preferred alkali or alkaline earth component when only a single component is selected for the composite of the invention.

Although it is possible for the catalyst of the invention to comprise only a single alkali or alkaline earth component it is possible for the alkali or alkaline earth component to comprise first and second alkali metal components. Both components are selected from the group consisting of cesium, rubidium, potassium, sodium and lithium; lithium as the first alkali metal, and potassium as the second alkali metal, however, are preferred. We believe that the alkali and alkaline earth component exists in the final catalytic composite in an oxidation state above that of the elemental metal. The alkali and alkaline earth component may be present as a compound such as the oxide, for example, or combined with the carrier material or with the other catalytic components.

Preferably, the alkali and alkaline earth component is well dispersed throughout the catalytic composite. The alkali or alkaline earth component generally will comprise about 0.01 to 15 wt. %, calculated on an elemental basis of the final catalytic composite. When the alkali and alkaline earth component comprises first and second alkali metal, it generally will comprise from about 0.05 to about 2.0 wt. % of the first alkali metal, and from about 0.05 to about 10.0 wt. % of the second alkali metal, calculated on an elemental basis of the final catalytic composite. In such instances the catalyst preferably comprises from about 0.05 to about 2.0 wt. % lithium and from about 0.05 to about 3.0 wt. % potassium.

The alkali or alkaline earth component may be incorporated in the catalytic composite in any suitable manner such as, for example, by coprecipitation or cogelation, by ion exchange or impregnation, or by like procedures either before, while or after other catalytic components are incorporated. A preferred method of incorporating the first and second alkali components is to impregnate the carrier material with a solution of potassium chloride and lithium nitrate.

The carrier material of the present invention is alumina having a surface area of from 5 to 150 m$^2$/g. The alumina carrier material may be prepared in any suitable manner from synthetic or naturally occurring raw materials. The carrier may be formed in any desired shape such as spheres, pills, cakes, extrudates, powders, granules, etc., and it may be utilized in any particle size. A preferred shape of alumina is the sphere. A preferred particle size is about 1/16 inch in diameter, though particles as small as about 1/32 inch, and smaller, may also be utilized.

To make alumina spheres, aluminum metal is converted into an alumina sol by reacting it with a suitable peptizing acid and water, and then dropping a mixture of the sol, a precursor of the Group IVA metal component and a gelling agent into an oil bath to form spherical particles of an alumina gel containing co-formed Group IVA metal component which are easily converted into the preferred gamma- or eta-alumina carrier material by known methods including aging, drying and calcining. Other shapes of the alumina carrier material may also be prepared by conventional methods. After the alumina particles containing co-formed Group IVA metal component are shaped, they are dried and calcined.

As indicated heretofore, the novel alumina support having a surface area of from 5 to 150 m$^2$/g has a pore structure such that less than about 18% of the total pore volume of the support is associated with pores having mean diameters of about 300 Angstroms or less and more than about 55% of the total pore volume associated with pores having mean diameters of about 600 Angstroms or more. It is believed that this novel pore structure results in improved catalyst performance by enhancing intra-particle diffusion. The enhanced diffusion is believed to result from the increase in the amount of pore volume associated with pores having mean diameters of about 600 Angstroms or more. However, it is advantageous to have some pore volume associated with micropores (pores having mean diameters of about 300 Angstroms or less) to assure sufficient catalyst surface area of from 5 to 150 m$^2$/g.

It is to be understood that the pore volume distributions set forth in the description of the invention and the appended claims are derived by the well-known mercury intrusion technique. This method may be used for determining the pore size distribution and pore surface area of porous substances by mercury intrusion using a Micromeritics Auto Pore 9200 Analyzer. In this method high pressure mercury is forced into the pores of the catalyst particles at incrementally increasing pressures to a maximum of 413,700 kPa (60,000 psia). Pore volume readings are taken at predetermined pressures. A maximum of 85 pressure points can be chosen. Accordingly by this method, a thorough distribution of pore volumes may be determined.

The alumina support of the present invention may be prepared by subjecting a precalcined alumina support to a recalcination step. As indicated heretofore in preparing an alumina support, the support is typically calcined and dried. However, it has been discovered that the novel pore distribution of the present invention may be induced by a recalcination step performed subsequent to the initial calcination. Accordingly, an alumina support containing co-formed Group IVA metal component is subjected to a calcination step conducted at from about 800° to about 1200° C. The calcination may be conducted in air, steam, or a mixture thereof. When a mixture is employed generally the steam will comprise from 1% to 50%.

The catalytic composite of our invention may also contain a halogen component. The halogen component may be either fluorine, chlorine, bromine or iodine or mixtures thereof. Chlorine and bromine are the preferred halogen components. The halogen component is generally present, we believe, in a combined state with the porous carrier material and alkali component. Preferably, the halogen component is well dispersed throughout the catalytic composite. The halogen component may comprise from more than 0.01 wt. % to about 15 wt. %, calculated on an elemental basis, of the final catalytic composite.

The halogen component may be incorporated in the catalytic composite in any suitable manner, either during the preparation of the carrier material or before, while or after other catalytic components are incorporated. For example, the alumina sol utilized to form the preferred aluminum carrier material may contain halogen and thus contribute at least some portion of the halogen content in the final catalyst composite. Also, the halogen component or a portion thereof may be added to the catalyst composite during the incorporation of the carrier material with other catalyst components, for example, by using chloroplatinic acid to impregnate the platinum component. Also, the halogen component or a portion thereof may be added to the catalyst composite by contacting the catalyst with the halogen or a compound or solution containing the halogen before or after other catalyst components are incorporated with the carrier material. Suitable compounds containing the halogen include acids containing the halogen, for example, hydrochloric acid. Or, the halogen component or a portion thereof may be incorporated by contacting the catalyst with a compound or solution containing the halogen in a subsequent catalyst regeneration step. In the regeneration step carbon deposited on the catalyst as coke during use of the catalyst in a hydrocarbon conversion process is burned off the catalyst and the platinum group component on the catalyst is redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound or solution containing the halogen, such as propylene dichloride, for example, to the hydrocarbon feed stream or to the recycle gas during operation of the hydrocarbon conversion process.

Optionally, the catalyst of our invention may also contain a sulfur component. Generally, the sulfur component may comprise about 0.01 to 2 wt. %, calculated on an elemental basis, of the final catalytic composite. The sulfur component may be incorporated into the catalytic composite in any suitable manner. Preferably, sulfur or a compound containing sulfur such as hydrogen sulfide or a lower molecular weight mercaptan, for example, is contacted with the catalyst composite in the presence of hydrogen at a hydrogen to sulfur ratio of about 100 and a temperature of from about 10° to about 540° C., preferably under water-free conditions, to incorporate the sulfur component.

Optionally, the catalyst may also contain other, additional components or mixtures thereof which act alone or in concert as catalyst modifiers to improve catalyst activity, selectivity or stability. Exemplary catalyst modifiers include those of group IIIA including gallium, indium and thallium which may be employed in an amount of from about 0.01 to about 5.0 weight percent based on the weight of the catalytic composite. These additional components may be added in any suitable manner to the carrier material during or after its preparation, or they may be added in any suitable manner to the catalytic composite either before, while or after other catalytic components are incorporated.

Preferably, the catalyst of our invention is nonacidic. "Nonacidic" in this context means that the catalyst has very little skeletal isomerization activity, that is, the catalyst converts less than 10 mole % of butene-1 to isobutylene when tested at dehydrogenation conditions and, preferably, converts less than 1 mole %. The acidity of the catalyst can be decreased if necessary to make the catalyst nonacidic by increasing the amount of the alkali component within the claimed range, or by treating the catalyst with steam to remove some of the halogen component.

After the catalyst components have been combined with the support material, the resulting catalyst composite will generally be dried at a temperature of from about 100° to about 320° C. for a period of typically about 1 to 24 hours or more and thereafter calcined at a temperature of about 320° to about 600° C. for a period of about 0.5 to about 10 or more hours. Finally, the calcined catalyst composite is typically subjected to a reduction step before use in the hydrocarbon conversion process. This reduction step is effected at a temperature of about 230° to about 650° C. for a period of about 0.5 to about 10 or more hours in a reducing environment, preferably dry hydrogen, the temperature and time being selected to be sufficient to reduce substantially all of the platinum group component to the elemental metallic state.

According to one process of our invention, dehydrogenatable hydrocarbons are contacted with the catalytic composite of our invention in a dehydrogenation zone maintained at dehydrogenation conditions. This contacting may be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then passed into the dehydrogenation zone containing a fixed bed of the catalyst. The dehydrogenation zone may itself comprise one or more separate reaction zones with heating means therebetween to ensure that the desired reaction temperature can be maintained at the entrance to each reaction zone. The hydrocarbon may be contacted with the catalyst bed in either upward, downward or radial flow fashion. Radial flow of the hydrocarbon through the catalyst bed is preferred for commercial scale reactors. The hydrocarbon may be in the liquid phase, a mixed vapor-liquid phase or the vapor phase when it contacts the catalyst. Preferably, it is in the vapor phase.

Hydrocarbons which may be dehydrogenated include dehydrogenatable hydrocarbons having from 2 to 30 or more carbon atoms including paraffins, alkylaromatics, naphthenes and olefins. One group of hydrocarbons which can be dehydrogenated with the catalyst is the group of paraffins having from 2 to 30 or more carbon atoms. The catalyst is particularly useful for dehydrogenating paraffins having from 2 to 15 or more carbon atoms to the corresponding mono-olefins or for dehydrogenating mono-olefins having from 3 to 15 or more carbon atoms to the corresponding di-olefins.

Dehydrogenation conditions include a temperature of from about 400° to about 900° C., a pressure of from about 0.01 to 10 atmospheres and a liquid hourly space velocity (LHSV) of from about 0.1 to 100 hr.$^{-1}$. Generally for paraffins the lower the molecular weight the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenation hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while or after being passed to the dehydrogenation zone. The diluent material may be hydrogen, steam, methane, ethane, carbon dioxide, nitrogen, argon and the like. Hydrogen is the preferred diluent. Ordinarily, when hydrogen is utilized as the preferred diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins having from 6 to 30 or more carbon atoms.

To be commercially successful a dehydrogenation catalyst should exhibit three characteristics, namely high activity, high selectivity and good stability. Activity is a measure of the catalyst's ability to convert reactants into products at a specific set of reaction conditions, that is, at a specified temperature, pressure, contact time and concentration of diluent such as hydrogen, if any. For dehydrogenation catalyst activity we measured the conversion or disappearance of paraffins in percent relative to the amount of paraffins in the feedstock. Selectivity is a measure of the catalyst's ability to convert reactants into the desired product or products relative to the amount of reactants converted. For catalyst selectivity we measured the amount of olefins in the product, in mole percent, relative to the total moles of the paraffins converted. Stability is a measure of the rate of change with time on stream of the activity and selectivity parameters—the smaller rates implying the more stable catalysts. In the following examples the particular characteristic of interest is selectivity.

The following examples are introduced to further describe the catalyst and process of the invention. The examples are intended as illustrative embodiments and should not be considered to restrict the otherwise broad interpretation of the invention as set forth in the claims appended hereto.

BRIEF DESCRIPTION OF THE DRAWING

FIG. 1 is a graph of the selectivities of the catalysts in weight percent for producing normal olefins as a function of normal paraffin conversion in weight percent.

EXAMPLE I

Figure 1:
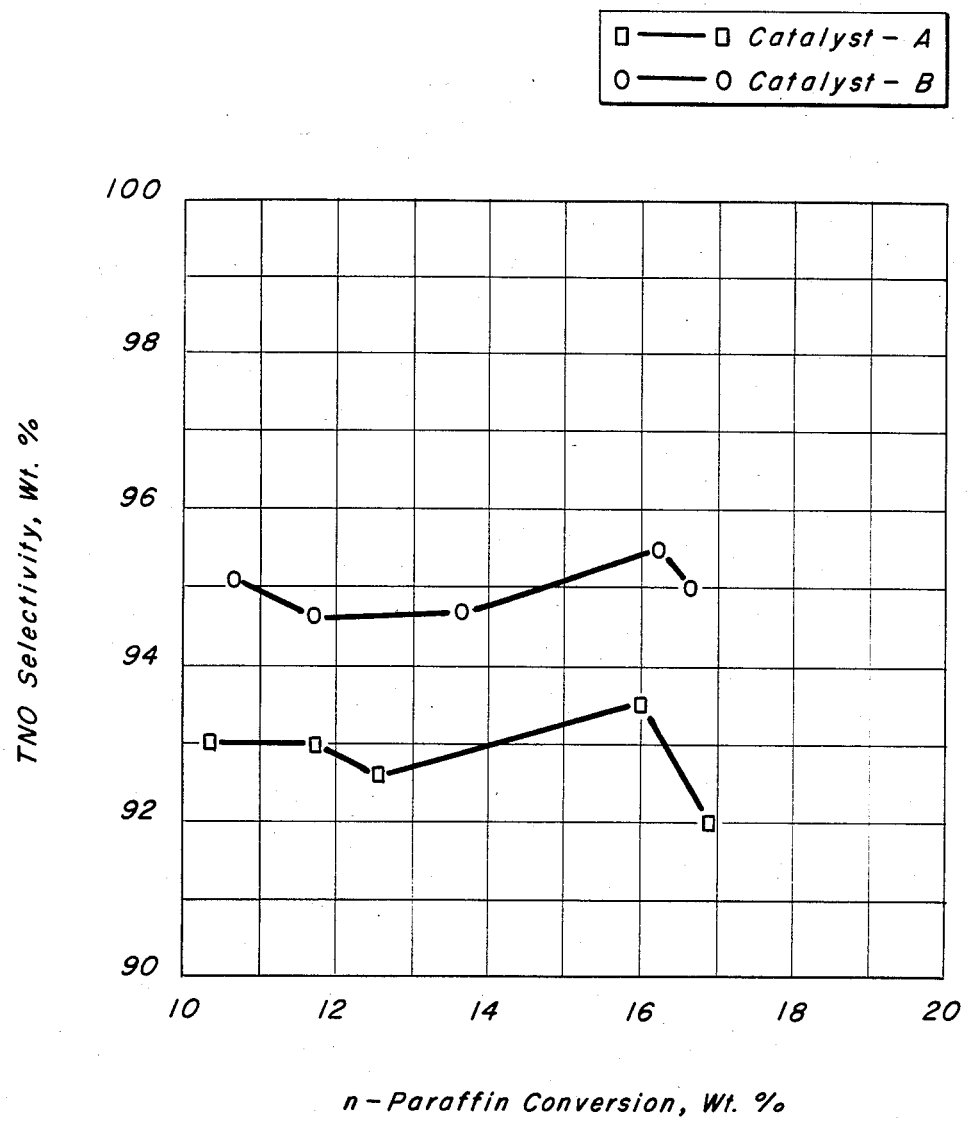
FIG. 1 is a graphical representation of the performance in a paraffin dehydrogenation process of Catalyst A, different from the invention, and Catalyst B, in accordance with the invention.

A catalyst support comprising alumina and a tin component was prepared by means of cogelation. This support was calcined at a temperature of about 677° C. for about 1.5 hours. Thereafter a portion of the catalyst was contacted with an impregnation solution in a rotary evaporator. The impregnation solution comprised an aqueous mixture of $H_2P+Cl_6$, $LiNO_3$ and $HNO_3$. The support and impregnation solution were rolled until all the impregnation solution was evaporated. This took about 2 hours. Thereafter the impregnated catalyst was dried in an oven at about 150° C. for 2 hours. The dried catalyst was then subjected to a calcination step in flowing air at about 540° C. for about 2½ hours. The catalyst was then cooled to about 180° C. and then subjected to a reduction step in hydrogen at about 500° C. for 2 hours. The resulting catalyst was designated Catalyst A. Catalyst A comprised about 0.38 wt. % platinum, about 0.6 wt. % lithium, about 0.5 wt. % tin, and about 0.1 wt. % chlorine. The catalyst support had an apparent bulk density (ABD) of about 0.295 g/cc and a surface area of 184 m²/g. The catalyst had a pore volume distribution such that about 20.7% of the total pore volume of the support was associated with pores having mean diameters of about 300 Angstroms or less and about 52% of the total pore volume of the support was associated with pores having mean diameters of about 600 Angstroms or more. Thus, Catalyst A was not in accordance with the invention.

EXAMPLE II

In this example a catalyst was prepared substantially as set forth above. However, in this case a catalyst support comprising a cogelled Group IVA metal component and alumina was subjected to a second calcination step subsequent to the first calcination step at 677° C. and prior to impregnation with the other catalytic metals. This second calcination step was effected at a temperature of about 903° C. in an atmosphere of about 31% steam and 69% air. This second calcination step took place for 3 hours. Following the second calcination step the support was impregnated substantially as in Example I above.

This second catalyst was designated Catalyst B. Catalyst B comprised about 0.38 wt. % platinum, about 0.60 wt. % lithium, about 0.50 wt. % tin, and about 0.1 wt. % chlorine. Catalyst B had an ABD of about 0.298 and a surface area of about 80 m²/g. The pore volume distribution was such that about 11.8% of the total pore volume of the support was associated with pores having mean diameters of less than about 300 Angstroms or less, and about 60% of the total pore volume of the support was associated with pores having mean diameters of 600 Angstroms or more. Thus Catalyst B was made in accordance with the invention.

It should be noted that the only distinction in preparation of the catalyst supports of Catalysts A and B is the fact that Catalyst B was subjected to a second calcination step prior to impregnation with the balance of the catalytic metals. Notwithstanding this second calcination step the change in the ABD between Catalyst A and Catalyst B was only 0.004. By way of contrast, the change in ABD observed upon a second calcination in aforementioned prior art reference, U.S. Pat. No. 4,070,413, was much greater, 0.026 for Catalyst B and 0.022 for Catalyst C of the reference. The Group IVA metal component in Catalysts B and C of the reference was coimpregnated and not co-formed as in the present invention.

EXAMPLE III

In the example Catalysts A and B were evaluated as catalysts for the dehydrogenation of normal paraffins. These evaluation tests were carried out in a pilot plant comprising a reactor and product separation facilities.

A charge stock was passed into the reaction zone wherein it was contacted with the catalyst. The effluent from the reaction zone was thereafter separated and analyzed. The charge stock comprised a mixture of normal paraffins having the following composition;

| COMPOSITION OF FEED | |
|---|---|
| $C_9$ n-paraffins | 0.1 wt. % |
| $C_{10}$ n-paraffins | 11.4 wt. % |
| $C_{11}$ n-paraffins | 26.0 wt. % |
| $C_{12}$ n-paraffins | 33.3 wt. % |
| $C_{13}$ n-paraffins | 26.7 wt. % |
| $C_{14}$ n-paraffins | 0.1 wt. % |
| Non-normals | 2.4 wt. % |
| Total | 100.0 wt. % |

The reaction zone was maintained at a pressure of about 20 psig. The charge stock was passed to the reaction zone at a rate sufficient to produce a liquid hourly space velocity of about 70 hrs.$^{-1}$. Hydrogen diluent was fed to the reaction zone at a rate sufficient to provide a molar hydrogen to hydrocarbon ratio of about 4:1. The feedstock was heated to a temperature of about 495° C. prior to contact with the catalyst. The results of these tests are set forth in FIG. 1. FIG. 1 is a plot of total normal olefin (TNO) selectivity in weight percent as a function of the normal paraffin conversion in weight percent. The total normal olefin selectivity in weight percent is defined as the weight of charge stock component converted to the desired normal olefin product divided by the weight of the total amount of charge stock components undergoing some reaction. The normal paraffin conversion is defined as the weight of the component in the fresh feed which actually underwent some reaction divided by the total weight of the feed. A review of FIG. 1 clearly indicates that at a given normal paraffin weight percent conversion Catalyst B, in accordance with the invention, exhibits higher selectivity for the production of normal olefins than does Catalyst A, different from the invention. This surprising and unexpected result clearly indicates the advantage to be achieved by means of the present invention.

What is claimed is:

1. A catalytic composite comprising a Group VIII noble metal component, a co-formed IVA metal component, an alkali metal or alkaline earth metal component and an alumina support having a surface area of from 5 to 150 m²/g wherein less than about 18% of the total pore volume of the support is associated with pores having mean diameters of about 300 Angstroms or less and more than about 55% of the total pore volume of the support is associated with pores having mean diameters of about 600 Angstroms or more.

2. The catalytic composite of claim 1 further characterized in that the Group VIII noble metal component comprises a platinum component.

3. The catalytic composite of claim 1 further characterized in that the co-formed Group IVA metal component comprises a tin component.

4. The catalytic composite of claim 1 further characterized in that it further comprises a Group IIIA metal component.

5. The catalytic composite of claim 4 further characterized in that the Group IIIA metal component is an indium component.

6. The method of claim 1 further characterized in that the co-formed Group IVA metal component is co-gelled.

7. The catalytic composite of claim 1 further characterized in that it comprises an alkali metal component.

8. The catalytic composite of claim 1 further characterized in that it comprises a halogen component.

9. The catalytic composite of claim 8 further characterized in that the halogen component comprises a chlorine component.

10. The catalytic composite of claim 1 further characterized in that it comprises from about 0.01 to about 5.0 wt. % each of the Group VIII noble metal component and the co-formed Group IVA metal component, and from about 0.01 to about 15 wt. % of the alkali metal or alkaline earth metal component based on the weight of the composite.

11. The catalytic composite of claim 4 further characterized in that it comprises from about 0.01 to about 5.0 wt. % Group IIIA metal component based on the weight of the composite.

12. The catalytic composite of claim 8 further characterized in that it comprises from about 0.01 to about 15.0 wt. % halogen.

13. The catalytic composite of claim 7 further characterized in that the alkali metal component comprises a lithium component.

14. The catalytic composite of claim 7 further characterized in that the alkali metal component comprises a lithium component and a potassium component.

15. A method of preparing a catalytic composite comprising compositing a Group VIII noble metal component, a co-formed Group IVA metal component, an alkali metal or alkaline earth metal component and an alumina support having a surface area of from 5 to 150 m²/g wherein less than about 18% of the total pore volume of the support is associated with pores having mean diameters of about 300 Angstroms or less and more than about 55% of the total pore volume of the support is associated with pores having mean diameters of about 600 Angstroms or more.

16. The method of claim 15 further characterized in that alumina containing the co-formed Group IVA metal component is subjected to a steam calcination step at about 800° to about 1200° C. in an atmosphere selected from the group consisting of air, steam or mixture thereof thereby producing the alumina support.

17. The method of claim 16 further characterized in that the co-formed Group IVA metal component and alumina support are composited by cogelation.

18. The method of claim 15 further characterized in that the catalytic composite is composited with a halogen component.

19. The method of claim 16 further characterized in that the atmosphere comprises a mixture of steam and air.

* * * * *